United States Patent [19]

Baik et al.

[11] Patent Number: 5,700,832
[45] Date of Patent: Dec. 23, 1997

[54] ANTIANEMIC AGENT CONTAINING IRON AND DIFRUCTOSE

[75] Inventors: Bu Hyun Baik; Young Woo Lee, both of Seoul; Yong Bok Lee, Kwangju, all of Rep. of Korea

[73] Assignee: Daewon Pharm. Co., Ltd., Rep. of Korea

[21] Appl. No.: 544,105

[22] Filed: Oct. 17, 1995

[30] Foreign Application Priority Data

Oct. 19, 1994 [KR] Rep. of Korea .................. 94-26692

[51] Int. Cl.$^6$ .................. A61K 31/295; A61K 31/70; A61K 31/495; A61K 31/44; A61K 31/715

[52] U.S. Cl. .................. 514/502; 514/52; 514/53; 514/249; 514/345

[58] Field of Search .................. 514/53, 502, 52, 514/249, 345

[56] References Cited

U.S. PATENT DOCUMENTS

| | | | |
|---|---|---|---|
| 3,076,798 | 2/1963 | Mueller et al. | 514/53 |
| 3,086,009 | 4/1963 | Zuschek et al. | 514/53 |
| 3,275,514 | 9/1966 | Saltman et al. | 514/53 |

*Primary Examiner*—Raymond Henley, III
*Attorney, Agent, or Firm*—Nath & Associates; Gary M. Nath; Suet M. Chong

[57] ABSTRACT

According to the present invention, an antianemic agent for the treatment of anemia caused by iron-deficiency containing iron and difructose. Iron and difructose contained in the said antianemic agent may form a complex, and their appropriate molar ratio is within the scope of 1:0.5 to 1:1000.

Further, the antianemic agent in accordance with the present invention may additionally contain hematopoietics such as cyanocobalamine, pyridoxine hydrochloride, folic acid, etc.

4 Claims, 6 Drawing Sheets

● : Fe(III)-fructose complex (1:1000)

▼ : Fe(III)-ascorbate complex (1:1000)

■ : Fe(III)-difructose complex (1:1000)

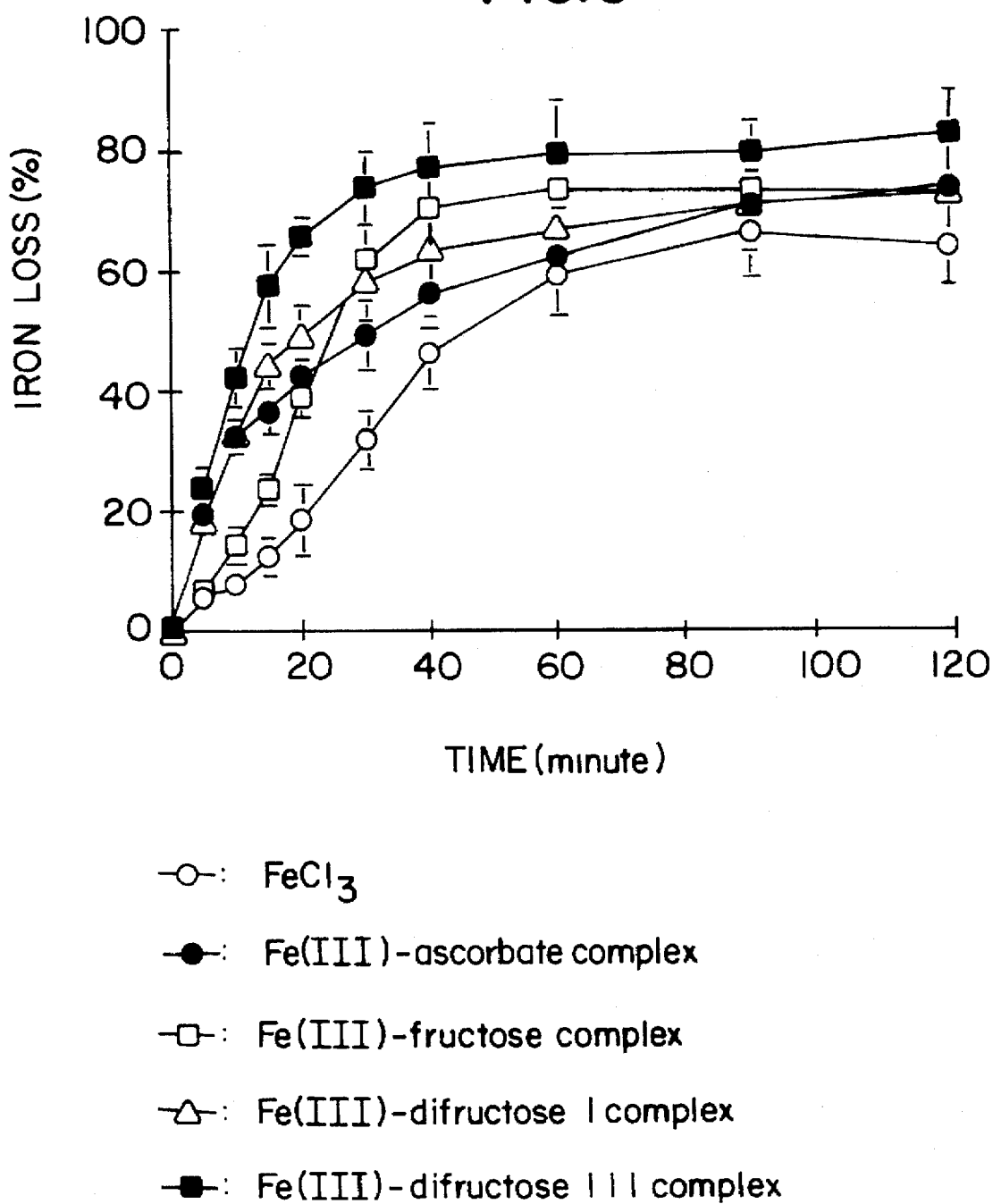

ANTIANEMIC AGENT CONTAINING IRON AND DIFRUCTOSE

TECHNICAL FIELD

The present invention relates to an antianemic agent effective in the treatment of iron deficiency anemias and more particularly, to an antianemic agent containing iron and difructose as it is or in the form of complex, thus increasing the iron absorption and decreasing the gastrointestinal disorders.

BACKGROUND ART

Anemia is a condition in which the concentration of the oxygen-carrying hemoglobin or red blood cells is below normal. The most common form of anemia is iron-deficiency anemia, comprising about 25% of all anemia-related patients. The causes of iron-deficiency anemia are diseases, diet that does not provide enough iron, or poor absorption of iron from diet. Another causes are extra needs in old people, children or pregnant women. Irrespective of the underlying causes, the complete treatment caused by iron-deficiency anemia relies on the administration of iron supplements but a prolonged therapy should be maintained until iron is stored in the body.

However, iron has a relatively low absorption rate of only about 5 to 15%. When absorbed and ionized in the body, iron preparations produces gastro-intestinal irritation, therefore upper abdominal pain, vomiting, diarrhea, etc. These irritant side-effects occur in 15 to 20% of orally administered patients but in these cases, the reduced drug compliance of patients may sometimes lead to the failure in the treatment of anemias. In this respect, to minimize these side-effects associated with iron preparations, it is recommended to reduce the contents of iron in the treatment of anemias, but this remains insufficient owing to a low absorption of iron.

The main site of iron absorption is duodenum and absorption is influenced by the following factors : 1) internal factors in the body, 2) iron concentration in the gastrointestinal lumen, 3) chemical form of iron administered, 4) pH of the gastrointestinal lumen, and 5) iron solubility in the gastrointestinal lumen.

To be free from the aforementioned defects related to a low absorption of iron and side-effects incurred out of the intake of iron preparations, many studies have been incessantly made to increase the iron solubility using some pharmaceutical additives such as ascorbic acid, citric acid, fructose, sorbitol, maltol, etc. [M. E. Conrad and S. G. Schade, Gastroenterology, 55(1), 35–45(1968), J. M. Hopping and W. S. Ruliffson, Am. J. Physiol., 210(6), 1316–1320(1966), C. Stitt, P. J. Charley, E. M. Butt and P. Saltman, Proc. Soc. Exper. Biol. Med., 110, 70–71(1962), G. Johnson and P. Jacobs, Exp. Hematol., 18(10), 1064–1069 (1990), M. A. Barrand, R. C. Hider and B. A. Callingham, J. Pharm. Pharmacol., 42(4), 279–282(1990), S. Pollak, R. M. Kaufman and W. H. Crosby, Blood, 24, 577(1964), P. J. Charley, C. Stitt, E. Shore and P. Saltman, J. Lab. & Clin. Med., 61(3), 397–410(1963)]

Among them, it was reported that ascorbic acid has been most widely recognized as a main chelating agent affecting on iron absorption. Ascorbate enhances the solubility by forming a complex salt with iron and act as reducing agent that prevents the oxidation of $Fe^{2+}$ to $Fe^{3+}$, which results in increasing iron absorption [M. E. Conrad et al., Gastroenterology, 55(1), 35–45(1968), J. M. Hopping and W. S. Ruliffson, Am. J. Physiol., 210(6), 1316–1320 (1966)].

Meantime, the process of manufacturing anti-anemic agent for treating anemia caused by iron-deficiency using polysaccharides and monosaccharides was disclosed in the U.S. Pat. No. 3,076,798, 3,086,009 and 3,275,514. According to the disclosure of Korean Patent Publication No. 76–124, a process of manufacturing complex salt of iron with dextrin for oral use in an effort to treat iron-deficiency anemia is disclosed. Nonetheless, it noted in its specification that the complex salt of iron and di-fructose was not satisfactorily formed.

Though many studies on iron absorption, and materials designed to promote the iron absorption have been reported, any iron preparations having better absorptivity and less side-effects have not been available thus far.

DISCLOSURE OF INVENTION

Under such circumstances, the present inventors have made intensive efforts to develop the substance to effectively promote the iron absorption, and have been aware that difructose, disaccharides consisting of fructose as natural saccharides, may significantly enhance the iron absorption to complete the invention.

Therefore, the primary object of the present invention is to provide an iron-deficiency antianemic agent containing iron and difructose, more desirably Fe(III)-difructose complex as an active ingredient, designed to promote the iron absorption.

The molar ratio of iron to difructose contained in antianemic agent according to the present invention is within the scope of 1:0.5 to 1:1,000, more desirably 1:0.5 to 1:10.

The following five kinds of difructose, in terms of their binding types are available in the present invention, but two kinds—difructose I and difructose III—were only employed in the Examples of the present invention. It is conceivable that the remaining kinds of difructose may be used for the agent promoting the iron absoption.

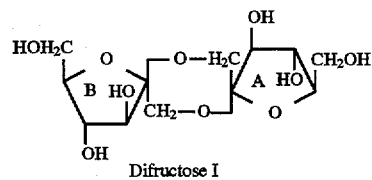

Difructose I

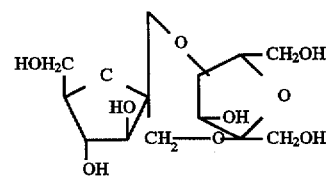

Difructose II

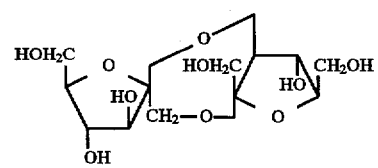

Difructose III

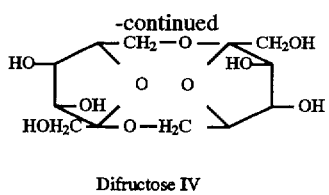

Difructose IV

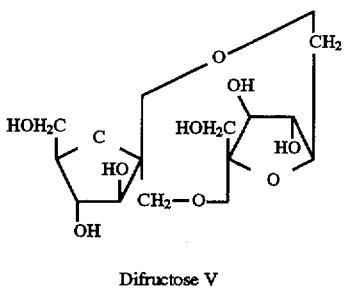

Difructose V

As set forth hereunder, the present invention has proven that difructose promotes the iron absorption.

The treatment for iron-deficiency anemia relies on the mechanism in which the iron absorbed in duodenal lumen should be transported to blood circulation. The iron transport mechanism across duodenum to blood may be considered by the following two steps:

the first step is that iron is absorbed within mucosal cells across brush-border membrane(BBM) of mucosal cells from the intestinal lumen and stored by binding with ferritin present in mucosal cells.

the second step is that iron, when depleted, is separated from ferritin and transported across basolateral membrane (BLM) of mucosal cell to capillary.

Therefore, this implies that in order to actually enhance the effects of iron absorption, the iron-absorption activator should play an role in not only increasing the iron absorption across the intestinal lumen to mucosal cell, but also in promoting the iron transport across the mucosal cell to capillary.

Said first step is known as the rate-limiting step in the systemic iron absorption. This invention has elucidated the effects of iron-complexes on the iron uptake by brush-border membrane vesicle(BBMVs). The BBMVs used for this experiment were collected from rat intestinal BBM (brush-border membrane) and prepared in a vesicle form to be easily employed in in-vitro absorption test[Experimental Example 1]. Through its enzyme and protein assay, it was confirmed that the vesicle was well purified. Electron microscopic appearance [FIG. 1] shows that the prepared vesicles were originated from the BBM and formed as a bilayer structure. It was also confirmed by D-glucose uptake test that the functional integrities of the BBM were well preserved. Therefore, the increase of the drug uptake by BBMVs reflects the increase of iron transport from intestinal lumen into mocosal cell which is considered as first step of the iron transport.

According to the present invention, complexes of iron with fructose, a kind of monosaccharide, and complexes of iron with difructose, a kind of disaccharide, were prepared. Through some uptake tests by BBMVs, their absorption patterns and degrees were measured. Then, the complexes were compared to Fe(III)-ascorbate complex, being already recognized to promote the iron absorption and thus it was proven that each complex of the present invention promotes the iron absorption in the first rate-limiting step of systemic absorption.

According to the present invention, to further investigate that the complexes of iron with fructose and difructose promote the iron absorption across the duodenal lumen in vivo, the loss of iron within duodenal lumen was measured. Then, the complexes were compared to Fe(III)-ascorbate complex, and thus it was proven that Fe(III)-difructose complex promotes the iron absorption in vivo in said first step.

Also, to investigate the effects of iron transport across the mucosal cell to blood in said second step, the remaining amounts of iron within mucosal cell was measured, when the complexes of iron with fructose and those with difructose were administered to duodenum in vivo. Further, the loss amount in duodenal lumen, retained amount within duodenal tissue and transported amount to the blood were reviewed. Thus, it was proven that fructose or difructose promoted the iron transport to the blood in said second step.

The antianemic agent of the present invention may be administered for an adult in a daily dose of approximately 20 mg to 300 mg as Fe(III), more desirably approximately 50 to 200 mg.

Except for active ingredients such as iron and difructose, the antianemic agent of the present invention may include some hematopoietics such as cyanocobalamine, pyridoxine or its salts, folic acid, etc.

The antianemia agent of the present invention may be administered in the form of such oral dosage forms as tablet, powder, granule, capsule, liquid, syrup and elixir, or given in the form of such parenteral dosage forms as injectable and suppository. In this case, the oral administration is more desirable.

The desired oral dosage form is tablet or capsule, which may contain the following common excipients such as binders (gelatin, sorbitol, tragacanth, polyvinyl pyrrolidone, etc.), fillers (lactose, sugar, corn starch, glycine, etc.), lubricants (magnesium stearate, talc, polyethylene glycol, silica, etc.), disintegrants (starch, etc.) and wetting agent (sodium lauryl sulfate, etc.).

The change-over from tablet to sugar-coated tablet, designed to modulate the dissolution and absorption rate in the gastrointestinal tract, may be available by using the commonly used pharmaceutically acceptable additives such as protective agents, flavoring agents and/or coloring agents such as sugar, cellulose or its derivatives, polyvinylpyrrolidone, calcium phosphonate, calcium carbonate, food dye, dyeing lacquer, aromatic agent, ferric oxide, pigment, etc.

In order to prepare injectable solution as a parenteral use, the active ingredients of the present invention is dissolved in distilled water and/or vehicles consisting of polyhydric fatty alcohols such as glycerine, propyleneglycol, polyethyleneglycol, etc.

BRIEF DESCRIPTION OF DRAWINGS

FIG. 1-A: 140,000 times / FIG. 1-B: 280,000 times).

FIG. 6 is a graph showing the loss(%) of iron-complexes prepared in Example 1 and Comparative Examples 1 and 2 from the duodenal lumen.

BEST MODE FOR CARRYING OUT THE INVENTION

Figure 1A:
FIG. 1 is a photograph of electron microscopy of BBMVs manufactured from Experimental Example 1(Magnification.

The iron-complexes of the present invention are described in more detail as set forth hereunder, in terms of processes for preparation of the complexes, uptake test by BBMVs, and in situ and in vivo absorption test as well as preparation examples.

Example 1: Preparation of Fe(III)-difructose complex

The complexes of Fe(III)-difructose I and Fe(III)-difructose III were prepared, respectively by the method of Conrad et al., who prepared Fe(III)-ascorbate complex [M. E. Conrad and S. G. Schade, Gastroenterology, 55(1), 35–45 (1968)].

The two complexes of Fe(III)-difructose I and Fe(III)-difructose III were prepared respectively, by adding 0.1-fold, 0.5-fold, 1-fold, 2-fold, 3-fold, 4-fold, 5-fold, 10-fold and 1,000-fold molar amount of difructose I and difructose III to $FeCl_3$ solution(5 μm) containing trace amount of $^{59}FeCl_3$ (0.0002 μCi/μl). After 10 min, the pH of the two iron-complex solutions was adjusted to 7.4 with 2N NaOH. The final concentration of Fe(III) was 5 μm, while the final concentrations of difructose I and difructose III were 0.5, 2.5, 5, 10, 15, 20, 25, 50 μM and 5 mM, respectively.

Comparative Example 1: Preparation of Fe(III)-D-fructose complex

In accordance with the same method as Example 1, Fe(III)-D-fructose complex was prepared. The final concentration of Fe(III) was 5 μM, while those of fructose were 0.5, 2.5, 5, 10, 15, 20, 25, 50 μM and 5 mM, respectively.

Comparative Example 2: Preparation of Fe(III)-ascorbate complex

In a same method as did in said Example 1, Fe(III)-ascorbate complex was prepared. After reacting $FeCl_3$ solution containing trace amounts of $^{59}FeCl_3$ (0.0002 μCi/μl) with ascorbic acid in acidic condition, the pH of the said solution was adjusted to 7.4. The final concentration of Fe(III) was 5 μM, while that of ascorbic acid was 5 mM.

Experimental Example 1: Preparation of BBMVs

The BBMVs were prepared from the entire small intestine of three male rats(Wister) and BBMVs were deep frozen until used. The isolation procedure was based upon the divalent cation precipitation method [H. Yuasa, G. L. Amidon and D. Fleisher, Pharm. Res., 10(3), 400–404(1993)], was slightly modified. All steps were performed on ice bath(4° C.).

Rats were killed by cervical dislocation. The intestines ranging from duodenum to ileum were immediately removed and rinsed with ice-cooled saline. The end of intestines tied were everted by a long wire, rinsed with ice-cooled saline and smoothly blotted by soft tissue to remove mucus. Then brush-border were scraped by thin plastics to be adjustable of a gap. The scrapings were made to be a 5%(v/v) homogenate by adding homogenization solution consisting of 0.1M D-mannitol and 1 mM Tris/HEPES, pH 7.4 and homogenized by warning blender homogenizer for 2 min at maximum speed. A solution of 1M $CaCl_2$ was added to make the final concentration be 20 mM, and the homogenate was stirred by vortex for 2 min and allowed to stand on ice for 20 min to precipitate intracellular organelles and basolateral membrane vesicle. The homogenate was centrifuged for 15 min at 4,200 rpm in a refrigerated centrifuge at 4° C. The supernatant was centrifuged for 30 min at 17,500 rpm in a high speed centrifuge. The resulting pellet was suspended in 30 ml of loading solution containing 100 mM mannitol and 100 mM HEPES/Tris (pH 7.5), and homogenized in a glass-Teflon homogenizer. A solution of 10 mM $CaCl_2$ was added to make the final concentration become 0.05 mM, and the solution was stand for 10 min and then centrifuged again for 15 min at 4,200 rpm. The supernatant was centrifuged for 30 min at 17,500 rpm. Finally, the BBMVs were isolated and purified. The BBMVs were resuspended in an appropriate amount of loading suspension to make the concentration 3–5 mg protein/ml and then dispersed through a syringe with 25 gauge needle.

To assess the degree of purity of BBMVs, p-nitrophenylphosphate as enzyme substrate was used to measure the specific activity of the marker enzyme, alkaline phosphatase, in the final preparations compared to the 5% homogenate. The reaction was initiated by the addition of prepared BBMVs and 200 μl of 5% homogenate to each solution consisting of 1.4 ml of enzyme substrate(50 mM) and 0.4 ml of $MgCl_2$(50 mM). The mixture was incubated at 37° C. for 5 min and the absorptivity of free p-nitrophenol was measured at 410 nm by UV/visible spectrophotometer. As a result, the specific activity of alkaline phosphatase in the finally prepared membrane vesicles was increased about 16-fold over the 5% homogenate, which reflects that BBMVs were well purified from 5% homogenate.

Further, to investigate some characteristics of the prepared BBMVs (surface, shape and size), the prepared vesicles were observed in an electron microscopy by the following negative staining method.

A formvar-coated copper grid was allowed to float on a drop of the BBMVs suspension (approximately 5 mg protein/ml) for 5 min. After removing excess liquid, the grid was then brought in contact with an aqueous solution of uranyl acetate(1%) for 30 sec., and blotted dry by contacting with 1% uranyl acetate solution for 30 min and examined in an electron microscope (Carl zeiss 109).

Figure 1B:
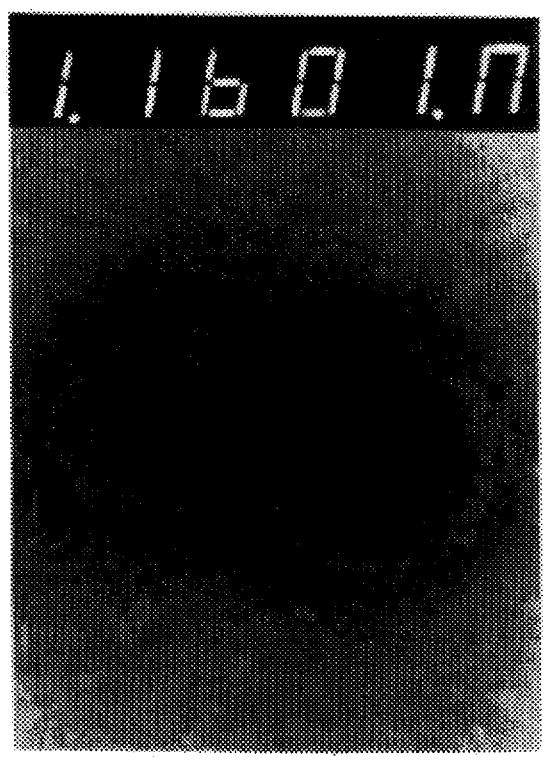

Electron microscopic appearance of the BBMVs is that under the negative staining method, most of the membrane vesicles were found with bilayer structures and also with a size approximately that of microvillus. Fibrous materials and other contaminants were virtually absent. The BBMVs prepared in accordance with this experiment was very well favorable and adequate in the uptake studies since no debris were found[FIG. 1].

To confirm the functional integrities of prepared BBMVs, the $Na^+$-dependent D-glucose uptake test, the most widely used method, was conducted with the rapid Millipore filtration [J. J. M. Marx and P. Aisen., Biochim. Biophys. Acta., 649, 297–304(1981)]. As a result, a typical overshooting uptake was initially observed in the presence of sodium ions and this implies that D-glucose uptake was dependent on sodium ions. Thus it was confirmed that the membrane was very well prepared as vesicles and the functional integrities of the BBM was very well preserved.

Experimental Example 2: Uptake of iron-complex by BBMVs

Figure 2:
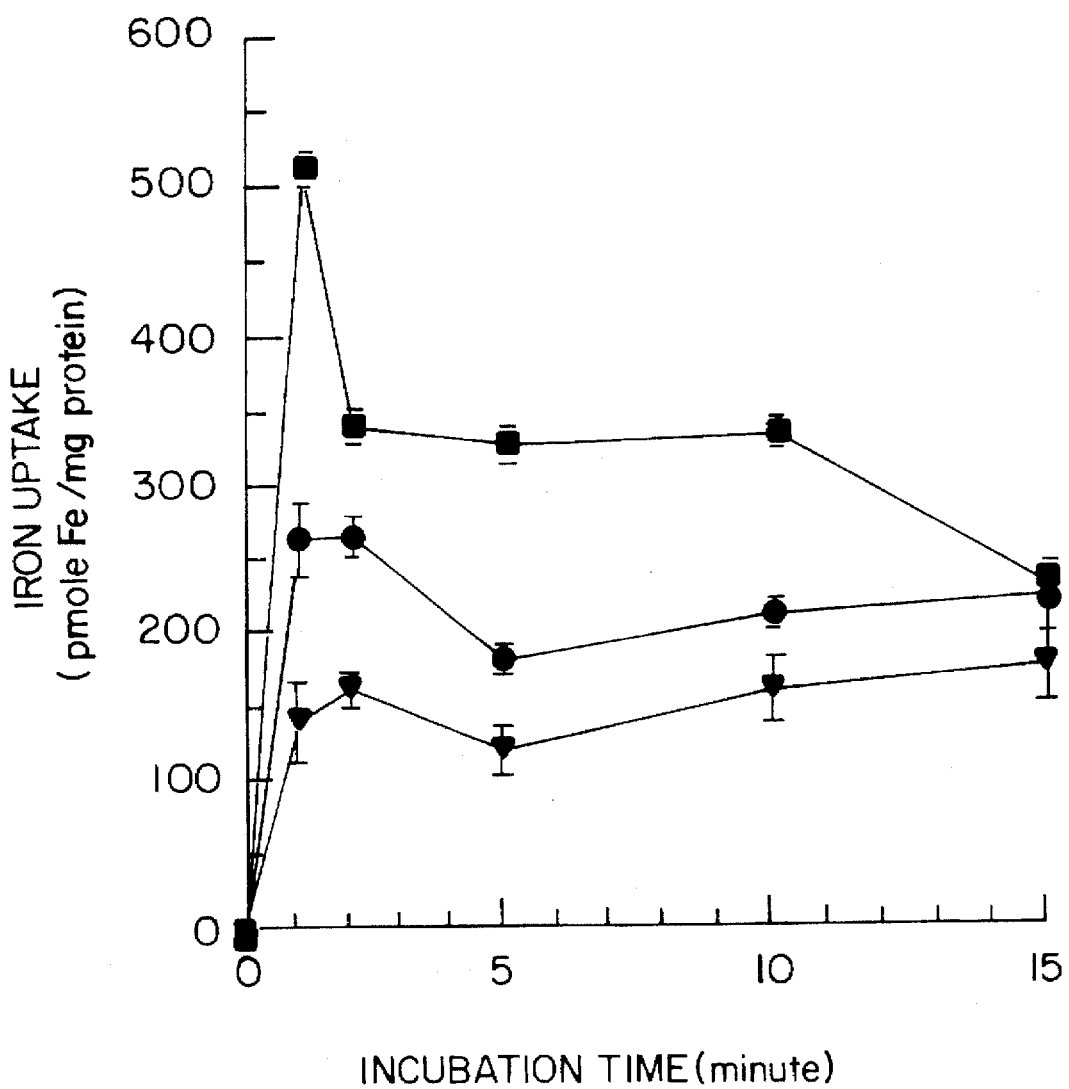
FIG. 2 is a graph showing the uptakes of iron complexes prepared in accordance with Example 1 and Comparative Example 1 & 2 into BBMVs.

To test the uptakes of the three iron complexes by BBMVs prepared in said experiment, i.e., Fe(III)-difructose III complex, Fe(III)-fructose complex and Fe(III)-ascorbate complex prepared in Example 1, and Comparative Example 1 and 2, respectively, the same rapid Millipore filtration technique as employed in $Na^+$-dependent D-glucose uptake test in Experimental Example 1 was conducted. As shown in FIG. 2, among the three iron-complexes prepared in same molar ratio (1:1000), there occurred the most rapid initial uptake by BBMVs in Fe(III)-difructose III complex, followed by Fe(III)-fructose complex and Fe(III)-ascorbate complex. After about 15 minutes, the uptakes of three iron-complexes were virtually in equilibrium.

The above results show that under the same condition, difructose III is more effective complex-forming material in view of promoting the iron absorption than fructose, and fructose more effective than ascorbate.

Figure 3:
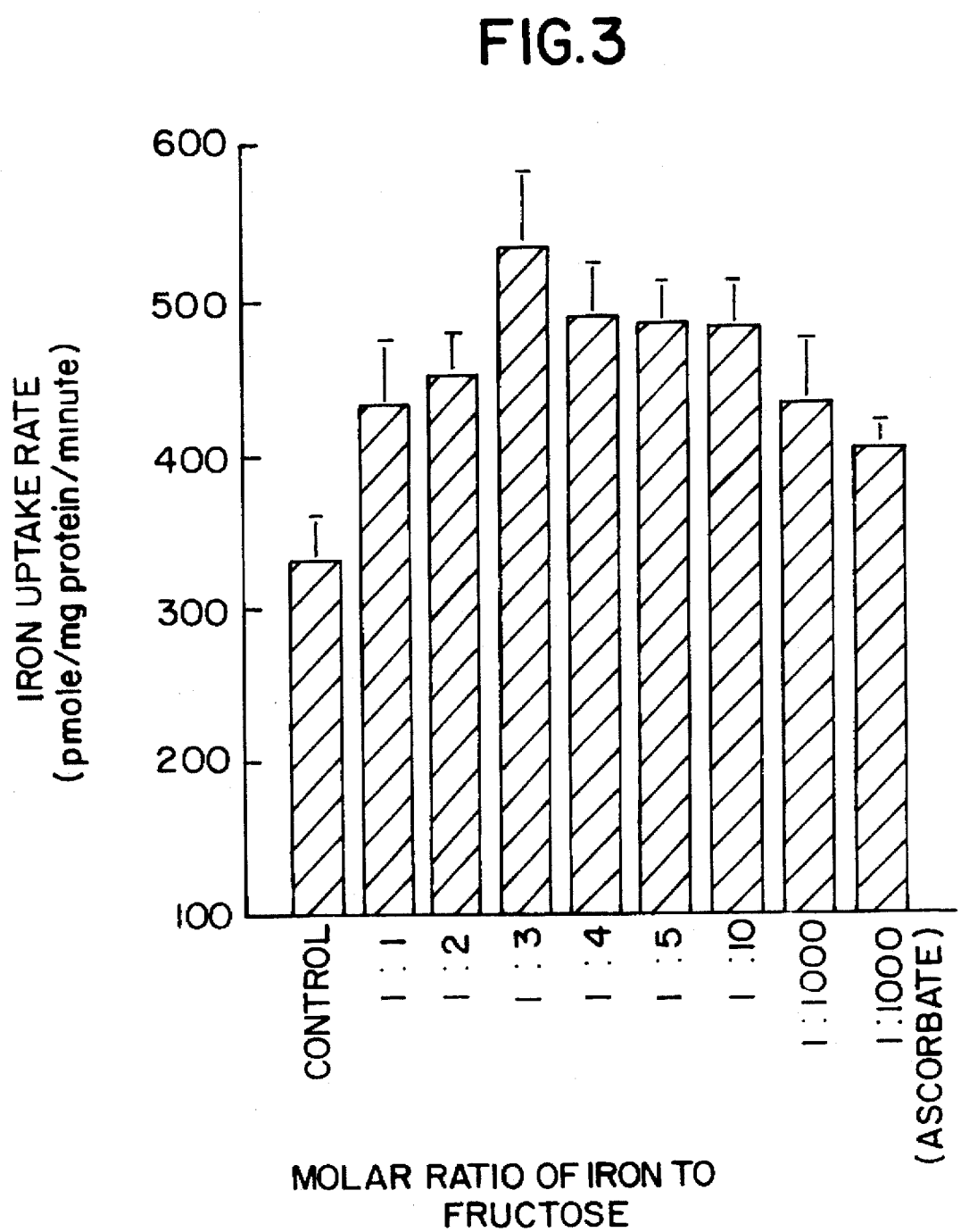
FIG. 3 is a graph showing the iron uptake of Fe(III)-fructose complex prepared in accordance with Comparative Example 1 into BBMVs with regard to molar concentration ratio.
Figure 4:
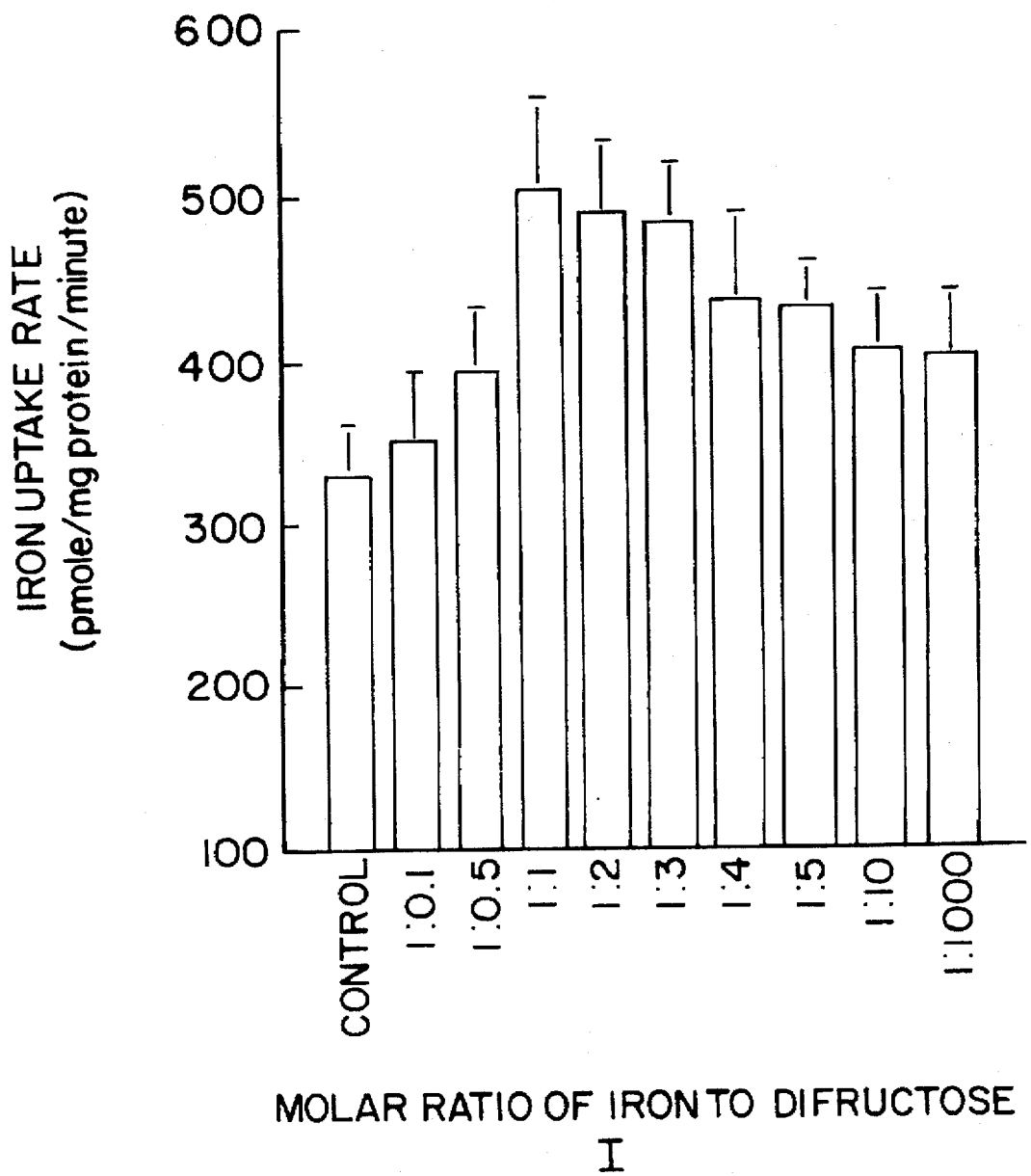
FIG. 4 is a graph showing the iron uptake of Fe(III)-difructose I complex prepared in accordance with Example 1 into BBMVs with regard to molar concentration ratio.
Figure 5:
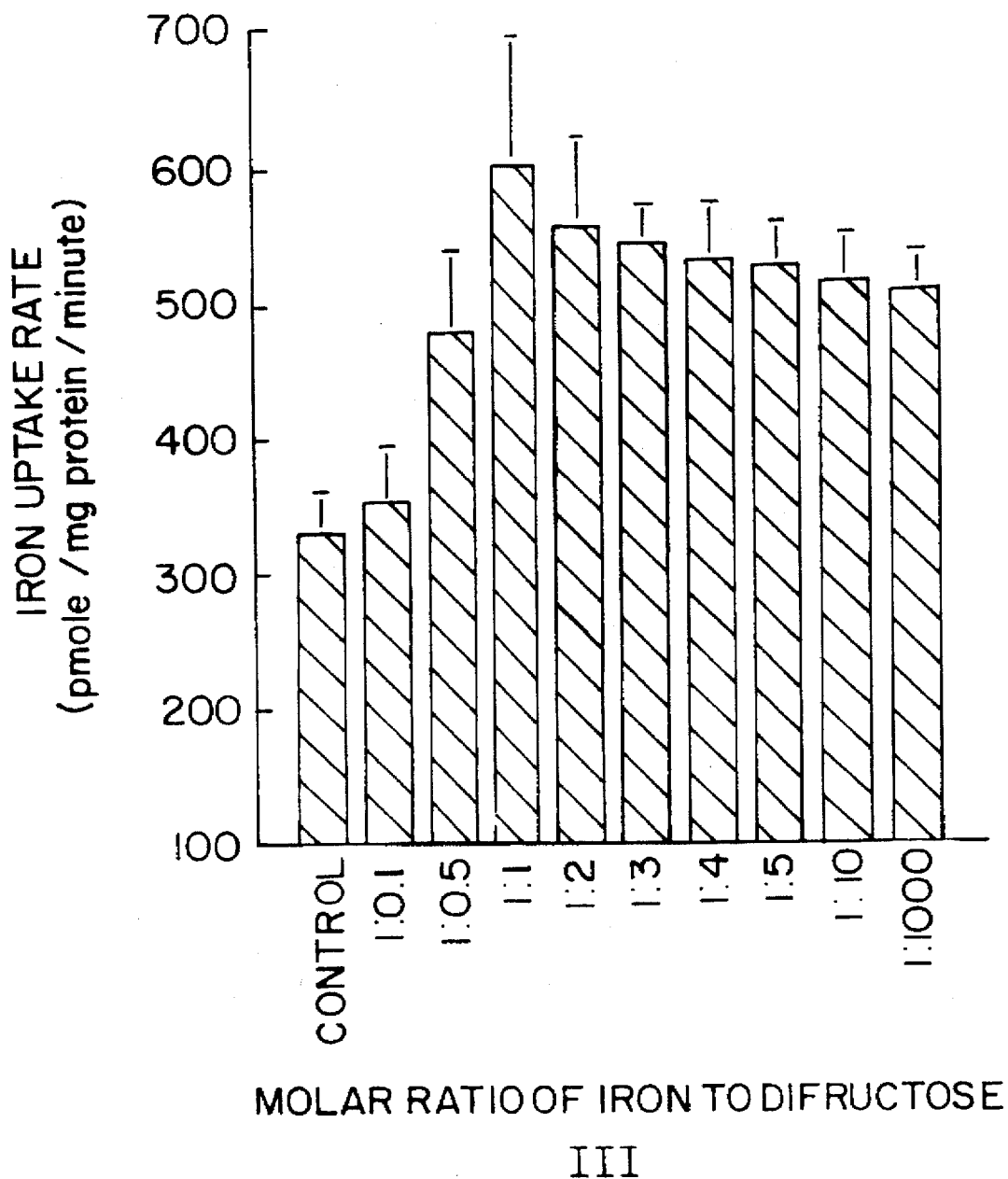
FIG. 5 is a graph showing the iron uptake of Fe(III)-difructose III complex prepared in accordance with Example 1 into BBMVs with regard to molar concentration ratio.

As shown in FIG. 3, FIG. 4 and FIG. 5, the uptake test by BBMVs for Fe(III)-fructose complex, Fe(III)-difructose I complex and Fe(III)-difructose III complex prepared with various molar ratio demonstrates that there exists an optimum molar ratio in which the most rapid uptake rate of iron by BBMVs is achieved. This appears that Fe(III)-difructose complex may be absorbed through same route as difructose absorbed within the gastrointestinal tract and iron in Fe(III)-difructose complex is absorbed together within the gastrointestinal tract. In case that the concentration of Fe(III) is much lower than that of difructose, the absorption of Fe(III)-difructose is, on the contrary, impeded by difructose. If the concentration of Fe(III) is higher than that of fructose, the lower ratio of complex formation leads to a smaller absorption.

The optimal molar ratios of prepared Fe(III)-fructose complex, Fe(III)-difructose I complex and Fe(III)-difructose III complex, showing the most rapid initial uptake rate of iron by BBMVs, were 1:3, 1:1 and 1:1, respectively. As presented in Table 1, the uptake rate of iron by BBMVs in each complex was about 1.6 times, 1.5 times and 1.8 times higher than that of iron by BBMVs when iron alone was given. This implies that the most rapid promotion of iron uptake by BBMVs was achieved by Fe(III)-difructose III complex in an optimal molar ratio(1:1).

TABLE 1

Maximum uptake ratio of iron-complexes by BBMVs

| Complex | Iron uptake rate (pmole/mg protein/min) |
|---|---|
| FeCl$_3$ (alone) | 330 ± 30 |
| Fe(III)-ascorbate (1:1000) | 396 ± 18 |
| Fe(III)-fructose (1:3) | 532 ± 47* |
| Fe(III)-difructose I (1:1) | 502 ± 56* |
| Fe(III)-difructose III (1:1) | 598 ± 92* |

* mean ± S.D. (n = 3–5), *p < 0.05

Experimental Example 3: Iron absorption test in situ and in vivo

Iron absorption tests in situ and in vivo were performed by the modified duodenum ligation loop method which had been used by Savin et al. and Campen in the test of iron absorption [M. A. Savin and U. D. Cook, Blood, 56(6), 1029–1035(1980); D. V. Campen, J. Nutr., 103, 139–142 (1973)].

After fasted for 24 hours, each animal of every experimental group consisting of 5 to 8 rats each was anesthetized with ether. The abdomen was opened by a middle incision and was removed the duodenum. The first three-way cock with silicone tube(Eyela, 2.7 mm i.d., Japan) was inserted at a distance of 5 cm from the pylorus while caring not to impair the blood vessel and the second three-way cock was further inserted at a distance of 20 cm from the first insertion site, and then the duodenum was ligated at both ends. The duodenum was slowly washed twice with irrigation solution to remove the substances within the duodenal lumen, and 5 ml of solution of Fe(III)-fructose, Fe(III)-difructose I and Fe(III)-difructose III in molar ratio showing the highest uptake rate of iron were given to each group of experimental animals through the first tube, in case the final concentration of Fe(III) is adjusted to be 100 μM [1 μCi $^{59}$Fe(III)]. Then, small amounts of the solution within the duodenal lumen were collected at 5, 10, 15, 20, 30, 40, 60, 90 and 120 minutes after the drug administration. After collecting the final specimen, the abdominal artery was rapidly excised and the animals were sacrificed by exsanguination. The ligated duodenum segment was excised and washed with predetermined amount of saline. The radioactivities contained in this saline solution together with those in the collected samples were measured by Gamma Counter (COBRA 5002, Packard Inst., Dowers Grove, Ill., U.S.A.), to acquire the amount of radioactivity retained in the duodenal lumen not absorbed in the duodenal tissue. Moreover, the amounts of iron retained in the duodenal tissue, which have not yet transported to the blood, were measured. Based on these values, the amount of iron loss from the duodenal lumen and the amounts of iron transported to the body (blood) were obtained by the following equation.

* iron loss=administered iron—iron retained in the duodenal lumen

* iron transported to the body(blood)=iron loss—iron retained in the duodenal tissue Meantime, under the same condition, a preliminary test using phenol red was conducted to correct the absorption of water. The excised ligation segment was placed on aluminum dish and dried at 105° C. for 48 hours to measure the dry weight, thus correcting the differences incurred out of the length in absorbed region.

FIG. 6 shows the change of iron loss with the lapse of time. In case of administrating Fe(III) alone, about 62% of iron was lost within 2 hr, while about 80% of iron was lost within 2 hr in case of Fe(III)-difructose III mixed in an optimal molar ratio. This implies that Fe(III)-difructose complex promotes the iron loss from the duodenal lumen.

However, excluding Fe(III)-difructose III complex, the absorptivity of other iron complexes—Fe(III)-ascorbate complex, Fe(III)-fructose complex and Fe(III)-difructose I complex—did not show any significant difference compared to that of Fe(III) used alone. This does not coincide with the fact that these iron-complexes promote the iron uptake by BBMVs. Considering the fact that after being absorbed from duodenal lumen into duodenal tissue cells iron is again transported to the capillary and blood, this discordance is owing to the influence of a storage rate in the duodenal tissue or transport rate into blood.

As presented in Table 2, the amounts of iron (transported rate, %) which passed through the duodenal tissue cell and transported to the blood was investigated. In case of administrating iron alone, 9.3% of administered iron was transported to the blood, while in case of administrating Fe(III)-difructose III complex 38.1% of administrated iron was transported(4.1 times increased compared to the case of iron alone was used), and in case of Fe(III)-difructose I 31.9% of the iron was transported(3.4 times increased compared to the case of iron alone was used). It is noted that the two complexes—Fe(III)-difructose III and Fe(III)-difructose I—have an effect of reducing the retained rate in the duodenal tissue cells, thus increasing the transport rate of absorbed iron to the blood by 4.1 times and 3.4 times, respectively.

However, when Fe(III)-fructose complex was administered, the amounts of iron across the duodenal tissue cells to the blood were only 16.1%, about 1.7 times higher than dose of iron alone. This implies that fructose increases the iron uptake by BBMVs and the iron loss from the duodenal lumen, while it has little influence on the storage rate of iron absorbed in the intestinal tissue cells, whereby the retained rate was not reduced.

As described above, Fe(III)-difructose complex (e.g. Fe(III)-difructose III complex or Fe(III)-difructose I complex) with molar ratio of 1:1 promotes the iron absorption across the duodenal lumen to duodenal tissue cells and the iron transport across the duodenal tissue cell to the blood, about 3.4 to 4.1 times compared to the case when iron alone was administered. Thus, the difructose is proper as a promoter of iron absorption for the treatment of anemia. Further, it is conceivable that if difructose is used as the promoter, it may reduce the used amount of iron to 1/3 to 1/4 fold whereby minimizing the possible side effects.

TABLE 2

Amounts of iron (%) transported to the blood

| Complex | Iron loss[1] | Iron retained in duodenal tissue | Iron transported to body (blood)[2] |
|---|---|---|---|
| FeCl$_3$ | 61.5 ± 6.6 | 52.2 ± 5.8 | 9.3 ± 1.0 |
| Fe(III)-ascorbate (1:1000) | 71.2 ± 6.9 | 49.5 ± 5.2 | 21.7 ± 2.2 |
| Fe(III)-fructose (1:3) | 70.5 ± 5.5 | 54.4 ± 8.2 | 16.1 ± 3.1 |
| Fe(III)-difructose I (1:1) | 70.0 ± 5.8 | 38.1 ± 4.9* | 31.9 ± 4.5* |
| Fe(III)-difructose III (1:1) | 79.9 ± 7.1* | 41.8 ± 4.3* | 38.1 ± 5.1* |

*Mean ± S.D. (n = 3–5), *p < 0.05
[1]Iron loss (%) = [1 − (retained amounts in duodenal lumen/iron administered)] × 100
[2]Iron transported (%) = iron loss (%) − iron retained in duodenal tissue (%)

Preparation Example 1: Tablets

In accordance with the conventional process, tablets each containig the following active ingredients were prepared.

| | |
|---|---|
| Fe(III)-difructose complex [in terms of Fe(III)] | 100 mg |
| Cyanocobalamine | 500 μg |
| Pyridoxine hydrochloride | 5 mg |
| Folic acid | 0.5 mg |

Preparation Example 2: Sugar-coated tablets

In accordance with the conventional process, the tablets prepared above were coated with coatings containing sugar and talc, and the resultant tablets were abraded with mixture of bees wax and carnauba wax to obtain sugar-coated tablets each weighing 500 mg.

Preparation Example 3: Capsules

The following components were intimately mixed and sieved, and then filled into hard gelatin capsules to provide capsules each containing 100 mg of Fe(III)-difructose.

| | |
|---|---|
| Fe(III)-difructose complex [in terms of Fe(III)] | 100 g |
| Cyanocobalamine | 400 mg |
| Folic acid | 0.45 g |
| Sodium lauryl sulfate | 30 g |
| Starch | 280 g |
| Lactose | 280 g |
| Magnesium sterate | 6 g |

What is claimed is:

1. An antianemic agent for the treatment of anemia caused by iron-deficiency, wherein the agent enhances iron absorption across the intestinal lumen to mucosal cell while promoting iron transport across the mucosal cell to capillary, and the agent consists of an iron and difructose complex having an iron to difructose molar ratio of between 1:0.5 to 1:1000, and optionally at least one hematopoietic.

2. An antianemic agent according to claim 1, wherein the molar ratio of iron to difructose is within the scope of 1:0.5 to 1:10.

3. An antianemic agent according to claim 1, which consists of said iron and difructose complex having an iron to difructose molar ratio of between 1:0.5 to 1:1000.

4. An antianemic agent according to claim 1, wherein the at least one hematopoietic is selected from the group consisting of cyanocobalamine, pyridoxine hydrochloride and folic acid.

* * * * *